United States Patent
Noh et al.

(10) Patent No.: US 7,368,266 B2
(45) Date of Patent: May 6, 2008

(54) METHOD FOR L-THREONINE PRODUCTION

(75) Inventors: Kap-Soo Noh, Seoul (KR); Yeong-Chul Kim, Seoul (KR); Jae-Yong Park, Seoul (KR); Dai-Chul Kim, Kyungki-do (KR); Jin-Ho Lee, Kyungki-do (KR); Seung-Han Ok, Busan (KR)

(73) Assignee: CJ Corporation (KR)

( * ) Notice: Subject to any disclaimer, the term of this patent is extended or adjusted under 35 U.S.C. 154(b) by 0 days.

(21) Appl. No.: 11/047,932

(22) Filed: Feb. 1, 2005

(65) Prior Publication Data

US 2005/0136518 A1 Jun. 23, 2005

Related U.S. Application Data

(63) Continuation-in-part of application No. 10/257,465, filed as application No. PCT/KR02/00230 on Feb. 14, 2002.

(30) Foreign Application Priority Data

Feb. 13, 2001 (KR) ................... 2001-6976

(51) Int. Cl.
- C12P 13/08 (2006.01)
- C12N 9/88 (2006.01)
- C12N 1/20 (2006.01)
- C12N 15/00 (2006.01)
- C07H 21/04 (2006.01)

(52) U.S. Cl. .............. 435/115; 435/106; 435/183; 435/232; 435/252.3; 435/252.33; 435/320.1; 536/23.1; 536/23.2

(58) Field of Classification Search ............ 435/106, 435/119, 183, 232, 252.1, 252.3, 252.33, 435/320.1, 115; 536/23.1, 23.2
See application file for complete search history.

(56) References Cited

U.S. PATENT DOCUMENTS

| 4,321,325 A | 3/1982 | Debabov et al. ............ 435/115 |
| 5,236,831 A | 8/1993 | Katsumata et al. ......... 435/106 |
| 5,538,873 A | 7/1996 | Debabov et al. ............ 435/115 |
| 5,939,307 A | 8/1999 | Wang et al. |

FOREIGN PATENT DOCUMENTS

| EP | 0 685 555 A1 | 12/1995 |
| EP | 0 723 011 A1 | 7/1996 |
| EP | 0 857 784 A2 | 8/1998 |
| EP | 1 179 597 A1 | 2/2002 |
| JP | 58-126789 | 7/1983 |
| JP | 59-31691 | 2/1984 |
| JP | 2-219582 | 9/1990 |
| JP | 2002-51787 | 2/2002 |
| KR | 1992-0008365 | 9/1992 |
| KR | 1994-0014793 | 7/1994 |
| WO | WO 01-27258 | 4/2001 |

OTHER PUBLICATIONS

Jin Ho et al. Journal of Microbiology and Biotechnology (1992), 2(4), 243-7 (ABSTRACT).*
Sugita et al. Applied Microbiology and Biotechnology (1989), 30(3), 290-3.*
Patek et al. Folia Microbial (Praha). 1993; 38(5): 355-9.*
Shio et al. Agricultural and Biological Chemistry, vol. 54 (1990), No. 12 pp. 3275-3282.*
Herman, T. J Biotechnol. Sep. 4, 2003;104(1-3):155-72.
"pBRINT-Ts: a plasmid family with a temperature-sensitive replicon, designed for chromosomal integration into the lacZ gene of *Escherichia coli*"; Authors: Sylvie Le Borgne, Beatriz Palmeros, Fernando Valle, Francisco Bolivar and Guillermo Gosset; ELSEVIER; GENE An International Journal on Genes and Genomes, vol. 223; 1998; pp. 213-219.
"L-Threonine production by L-aspartate-and L-homoserine-resistant mutant of *Escherichia coli*"; Authors: Satoru Furukawa Akio Ozaki and Toshihide Nakanishi; Applied Microbiology and Biotechnology, vol. 29; 1988; pp. 550-553.

* cited by examiner

*Primary Examiner*—Tekchand Saidha
*Assistant Examiner*—Christian L. Fronda
(74) *Attorney, Agent, or Firm*—Cantor Colburn LLP

(57) ABSTRACT

A method for producing L-threonine using a microorganism is provided. In the method, additional one or more copies of each of the phosphoenolpyruvate carboxylase (ppc) gene and the threonine operon are integrated into a particular site of the chromosomal DNA of a microorganism, while its inherent ppc gene and threonine operon remain. Accordingly, two or more ppc genes and threonine operons are included in the chromosomal DNA of the microorganism to thereby enhance the expression of the ppc gene encoding an enzyme to convert phosphoenolpyruvate to a threonine biosynthesis precursor, oxaloacetete, and the genes encoding enzymes involved in the synthetic pathway of threonine from oxaloacetate, including thrA (aspartokinasel-homoserine dehydrogenase), thrB (homoserine kinase), and thrC (threonine synthase), thereby markedly increasing L-threonine productivity.

3 Claims, 4 Drawing Sheets

SEQUENCE LISTING

<160> NUMBER OF SEQ ID NOS: 2

<210> SEQ ID NO 1
<211> LENGTH: 29
<212> TYPE: DNA

```
-continued

<213> ORGANISM: Artificial
<220> FEATURE:
<223> OTHER INFORMATION: primer

<400> SEQUENCE: 1
aggaattctt ccgcagcatt tgacgtcac                                     29

<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2
aggaagcttt tagccggtat tacgcatacc                                    30
```

METHOD FOR L-THREONINE PRODUCTION

CROSS-REFERENCE TO RELATED APPLICATIONS

The present application is a continuation-in-part of U.S. application Ser. No. 10/257,465, filed Oct. 11, 2002, which was the National Stage of International Application No. PCT/KR02/00230, filed Feb. 14, 2002, which claimed the benefit of Korean Patent Application No. 2001-6976, filed Feb. 13, 2001, which are herein incorporated by reference in their entirety.

BACKGROUND OF THE INVENTION

1. Field of the Invention

The present invention relates to the production of L-threonine involving microorganisms. More particularly, the present invention relates to a process for producing L-threonine with a high yield, in which additional one or more copies of the phosphoenolpyruvate carboxylase (ppc) gene and the threonine operon are inserted into a particular site of the chromosomal DNA of a microorganism, while its inherent ppc gene and threonine operon remain, to increase the expression of the ppc gene encoding an enzyme to convert phosphoenolpyruvate to oxaloacetate, which is a threonine biosynthetic precursor, and the expression of genes encoding enzymes engaged in the synthetic pathway of threonine from oxaloacetate, such as aspartokinaseI-homoserine dehydrogenase (thrA), homoserine kinase (thrB), and threonine synthase (thrC).

2. Description of the Related Art

L-threonine, a kind of essential amino acid, is widely used as an additive to animal fodder and food, and as fluids and synthetic materials for medical and pharmaceutical use. L-threonine is produced by fermentation using synthetic mutants derived from wild types of *Escherichia coli, Corynebacterium, Serratia,* and *Providencia.* These variant strains are known to include amino acid analogs, pharmaceutical-resistant mutants, and synthetic pharmaceutical-resistant mutants rendered auxotrophic for diaminopimelic acid, methionine, lysine, or isoleucine (Japanese Laid-open Patent Application No. hei 2-219582, *Appl., Microbiolo. Biotechnol.,* 29, 550-553 (1988), and Korean Patent Publication No. 92-8365).

A common approach to increase the level of expression of a particular gene uses a plasmid that gives a greater copy number to a microorganism in order to increase the number of genes in the microorganism (Sambrook et al., *Molecular cloning,* Second Edition, 1989, 1.3-1.5). A target gene is integrated into a plasmid, and the host microorganism is transformed with the recombinant plasmid to cause an increase in the number of genes in the host microorganism according to the copy number in the plasmid. A partial success in this type of approach to improve threonine productivity is reported in U.S. Pat. No. 5, 538,873. However, most technologies using such recombinant plasmids overexpress a particular gene, which is undesirable for the host microorganism, and causes a problem of plasmid instability so that the plasmid is lost during cultivation of the recombinant strain.

To address this problem, approaches to add antibiotics to culture media or to use an expression regulatory plasmid were suggested (Sambrook et al. *Molecular cloning,* Second Edition, 1989, 1.5-1.6 & 1.9-1.11). In using the expression regulatory plasmid to yield a particular product, cell cultivation is performed under non-expression conditions in the growth stage to reduce a load to the host microorganism and temporary expression is induced after full growth of the microorganism. However, most expression regulatory plasmids target protein synthesis. Producing primary metabolites is closely associated with the growth of microorganisms, so it is difficult to increase the yield of the primary metabolites unless target genes are expressed in the growth stage. The production of threonine, a primary metabolite, is such a case.

As an effort to compensate for this drawback, a particular threonine biosynthetic gene was incorporated into a chromosomal DNA to produce threonine (U.S. Pat. No. 5,939, 307). However, this approach replaces a chromosomal gene by an inducible promoter-substituted gene, which is hardly expected to markedly increase the expression of the threonine operon gene.

Therefore, unlike the conventional substitution method, the present inventors have inserted an additional ppc gene and threonine operon into a particular site (lacZ gene) of the chromosomal DNA while the original chromosomal gene of a host microorganism remains, and found that it provides dual effects as a result of the original chromosomal gene and the inserted ppc gene and threonine operone. Most current genetic engineering techniques applied to increase the yield of threonine are focused on the biosynthetic pathway, starting with oxaloacetate. However, the present invention involves also ppc, which is an oxaloacetate inducer enzyme acting in the preceding step, as well as the threonine biosynthetic enzymes to purposely guide the flow of carbons from phosphoenolpyruvate into the oxaloacetate synthetic pathway. The present invention also allows insertion of two or more copies of gene if necessary.

SUMMARY OF THE INVENTION

To solve the above-described problems, it is an object of the present invention to provide a high-yield L-threonine production method which eliminates problems of plasmid instability and microbial growth inhibition arising with recombinant plasmid bearing strains and at the same time increases the expression of the phosphoenolpyruvate carboxylase (ppc) gene and the threonine operon.

The object of the present invention is achieved by a method of producing L-threonine, comprising: constructing a recombinant chromosomal DNA integration vector comprising one or more copies of each of a phosphoenolpyruvate carboxylase gene and a threonine operon of a microorganism belonging to the *Escherichia* or *Corynebacterium* genus; transforming a microorganism belonging to the *Escherichia* or *Corynebacterium* genus with the recombinant chromosomal DNA integration vector to integrate the one or more additional copies into a particular site of the microorganism's chromosomal DNA while the microorganism's inherent phosphoenolpyruvate carboxylase gene and threonine operon remain; culturing the transformed microorganism with substrates to produce L-threonine; and isolating the produced L-threonine According to the present invention, by incorporating two or more copies of the ppc gene and the threonine operon into the chromosomal DNA, the levels of expression of the ppc gene, which encodes an enzyme to convert photophoenol pyruvate to a threonine synthetic precursor, oxaloacetate, and the genes of enzymes engaged in the threonine synthesis from oxaloacetate, such as thrA (aspartokinase I-homoserine dehydrogenase), thrB (homoserine kinase), and thrC(threonine synthase).

In the L-threonine production method according to the present invention, the sequences of the ppc gene and the threoine operon of *Escherichia* or *Corynebacterium* genus may be obtained from NCBI's GenBank (URL: www.ncbi.nlm.nih.gov/Genbank). For example, the accession numbers of several ppc gene and the threoine operon are as follows: *E. coli* ppc gene of Accession No. X05903, *C. glutamicum* ppc gene of Accession No. AB115089, *E. coli* thrABC of Accession No. J01706, and *C. glutamicume* thrC of Accession No. X56037, and *C. glutamicume* thrB of Accession No. Y00546. Further, the ppc gene and the threoine operon can be easily amplified and cloned according to the conventional primer designing methods and PCR reaction (Molecular Cloning Vol.2, Chapter 8). Briefly, the ppc gene and the threoine operon are amplified using a Taq polymerase, a PCR reaction buffer, and primers designed based on the above-obtained sequences, the PCR products are purified using a gel extraction kit, the purified PCR products are cloned into conventional vectors by digesting the both with the same restriction enzymes and ligating them with T4 DNA ligase.

In the L-threonine production method according to the present invention, any chromosomal DNA integration vectors that can transform a microorganism belonging to the *Escherichia* or *Corynebacterium* genus, for example, pBRINT-Ts vectors (Sylvie Le Beatriz et al., 1998, pBRINT-Ts, Gene., 223, pp. 213-219), may be used. Further, the recombinant chromosomal DNA integration vector comprising one or more copies of each of the phosphoenolpyruvate carboxylase gene and the threonine operon of an *Escherichia* or *Corynebacterium* genus can be easily constructed according to the conventional DNA recombination methods. Briefly, the ppc and thrABC are cloned into MCS of pBRINT by simultaneously or serially digesting with the same restriction enzymes and ligating them with T4 DNA ligase.

In the L-threonine production method according to the present invention, methods of transforming a microorganism with a chromosomal DNA integration vector are known to one of ordinary skill in the art (Sylvie Le Beatriz et al., 1998, pBRINT-Ts, Gene., 223, pp. 213-219). Therefore, it can be easily achieved by one of ordinary skill in the art to transform an *Escherichia* or *Corynebacterium* genus and integrate a foreign gene into a particular site of the microorganim's chromosomal DNA according to the conventional transforming methods. Briefly, target strains are transformed with the recombinant vectors using a heat-shock or electroporation method, and the transformants are selected on antibiotics plates.

In the L-threonine production method according to the present invention, methods of culturing a *Escherichia* or *Corynebacterium* genus to produce L-threonine are known to one of ordinary skill in the art (Appl., Microbiolo. Biotechnol., 29, 550-553 (1988)). Therefore, it can be easily achieved by one of ordinary skill in the art to culture the transformed *Escherichia* or *Corynebacterium* and isolate the produced L-threonine according to the conventional culturing methods (Molecular Cloining Vol.11.32-1.34). Briefly, the transformant cells are cultured in LB medium and harvested in a mid-exponential phase. The harvested cells are lysed, neutralized, and passed through a chromatography column.

According to the present invention, any microorganism capable of producing L-threonine, including *Escherichia coli*, *Corynebacterium*, *Serratia*, and *Providencia* can be used with the *Escherichia coli* being preferred.

It is preferable that the ppc gene and the threonine operon additionally inserted into the microorganism is derived from a microorganism (synthetic mutant) resistant to threonine analogs, lysine analogs, isoleucine analogs, and methionine analogs.

According to the present invention, the ppc gene and the threonine operon may be additionally inserted into any site of the chromosomal DNA, except for the original threonine operon, but preferably into the lacZ gene site.

In the L-threonine production method according to the present invention, it is preferable that a ppc gene obtained from the chromosome of a L-threonine producing *E.coli* strain, TF4076 (KFCC 10718), by polymerase chain reaction (PCR) and a threonine operon cloned from the same chromosome are inserted into the chromosome of the host *E.coli* strain TF4076.

1. Threonine Operon and Phosphoenolpyruvate Carboxylase Gene

The threonine operon and phosphoenol pyruvate carboxylate (ppc) gene used were cloned from the chromosome of TF4076 (Accession Number: KFCC10718, Korean Patent Application No. 90-22965) deposited with the Korean Culture Center of Microorganisms (KCCM). This strain is auxotrophic for methionine and resistant to threonine analogs (AHV: α-amino-β-hydroxyvaleric acid), lysine analogs (AEC: S-(2-aminoethyl)-L-cysteine), isoleucine analogs (α-aminobutyric acid) and methionine analogs (ethionine).

2. Integration Vector pBRINT-TsGm, a plasmid vector for use in chromosomal integration, was used (Sylvie Le Beatriz et al., 1998, pBRINT-Ts: *A plasmid family with a temperature-sensitive replicon, designed for chromosomal integration into the lacZ gene of Escherichia coli.*, Gene., 223, pp. 213-219). This vector has temperature sensitivity; it integrates the cloned genes of a plasmide into a site of the lacZ gene of the chromosomal DNA when cultured at 37° C. whereas the remaining plasmids in the plasma are lost when the cultivation temperature is raised to 44° C.

3. Recombinant Vector

The ppc gene derived from the chromosome of TF4076 by polymerase chain reaction (PCR) and the threonine operon derived from a vector cloned with the threonine operon, pAT94 (KCCM 10018, Korean Patent Application No. 92-24732), which had been deposited on Dec. 2, 1992 with the Korean Culture Center of Microorganisms (KCCM) under the Budapest Treaty, were cloned into BamH I and EcoR I sites of pBRINT-TsGm to construct a recombinant plasmid vector pGmTN-PPC. Strain TF4076 was transformed with the recombinant plasmid vector and then cultivated at 37° C. to induce integration of the cloned ppc gene and threonine operon into the site of lacZ gene of the chromosomal DNA. Then, the cultivation was continued at 44° C. to get rid of the remaining plasmids in the host strain.

4. Screening Method

Colonies that are resistant to gentamycin and sensitive to carbenicillin, and looks white, not blue, in a solid medium containing X-gal and IPTG were visually screened for recombinant strains. This screening method is based on the principle that integration of the ppc gene and the threonine operon into the lacZ gene of the chromosomal DNA inactivates the lacZ gene to lose its ability to decompose the chromophore X-gal.

These selected recombinant strains were compared with the host strain for threonine productivity. As a result, the host strain produced 20 g/L of threonine in 48 hours whereas pGmTN-PPC (Accession Number: KCCM-10236), one of the recombinant strains with the ppc gene and the threonine operon integrated into the chromosomal DNA, shows a highest threonine productivity at 27.0 g/L with a yield of about 35% (see Example 4). The pGmTN-PPC strain produces 102 g/l of threonine through fermentation in a 5-L fermentor with a higher yield of 35.4% than the host strain (see Example 5).

BRIEF DESCRIPTION OF THE DRAWINGS

The above object and advantages of the present invention will become more apparent by describing in detail exemplary embodiments thereof with reference to the attached drawings in which.

DETAILED DESCRIPTION OF THE INVENTION

The present invention will be described in greater detail by means of the following examples. The following examples are for illustrative purposes and are not intended to limit the scope of the invention.

EXAMPLE 1

Cloning of Phosphoenolpyruvate Carboxylase Gene

Figure 1A:
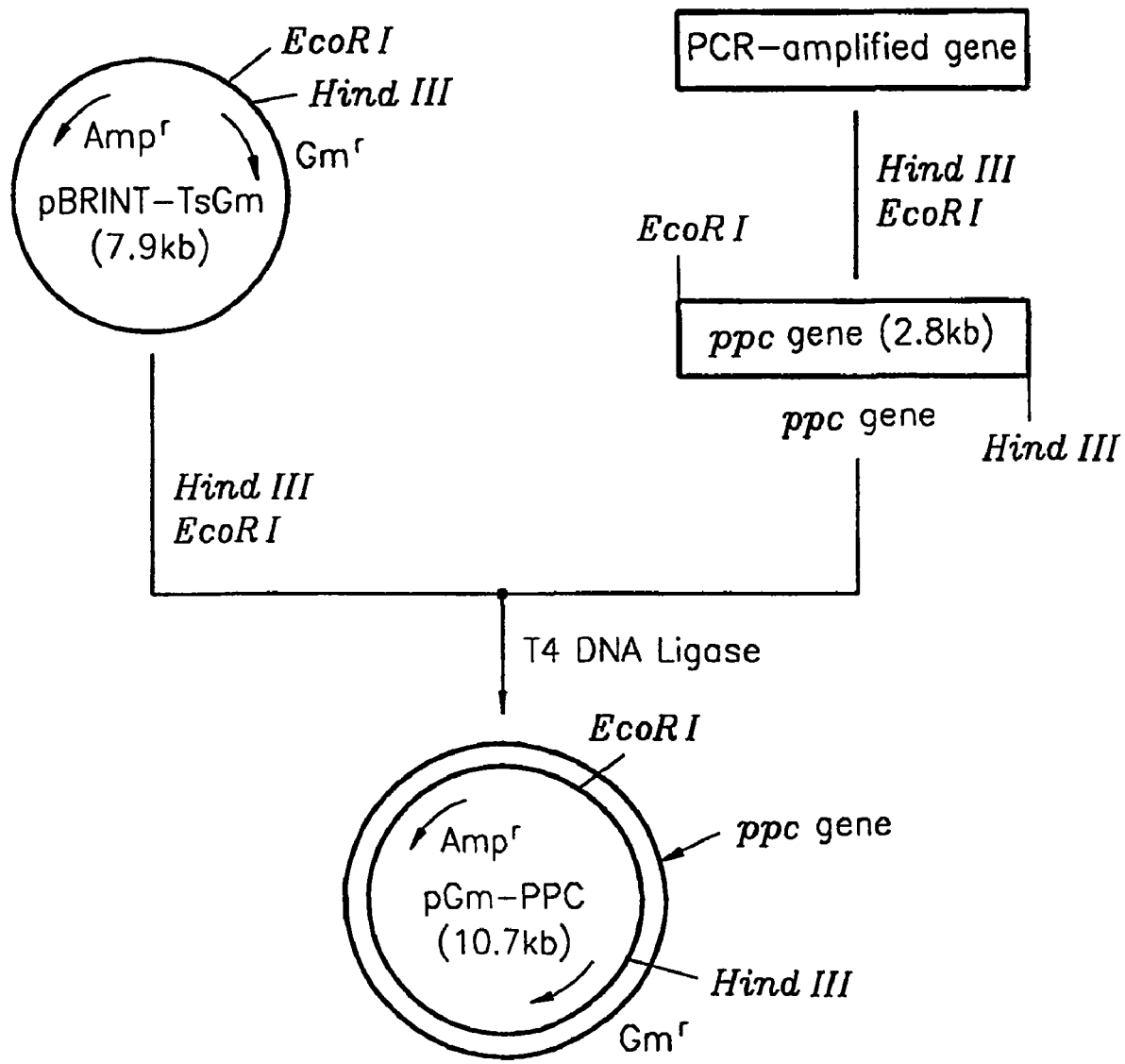
FIG. 1A depicts a process of cloning a phosphoenolpyruvate carboxylase (ppc) gene.
Figure 1B:
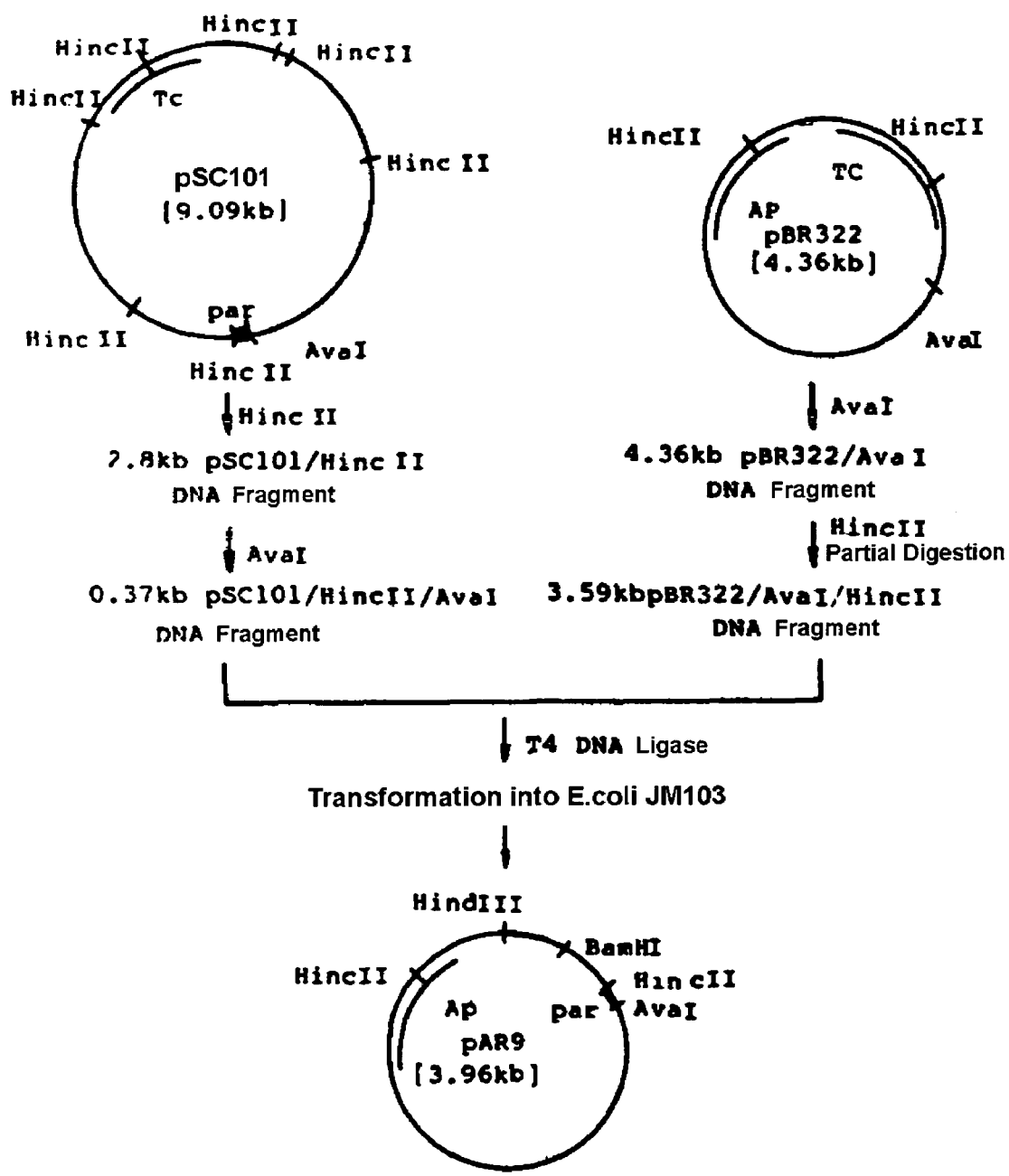
FIG. 1B depicts a process of constructing a recombinant plasmid pAR9.
Figure 1C:
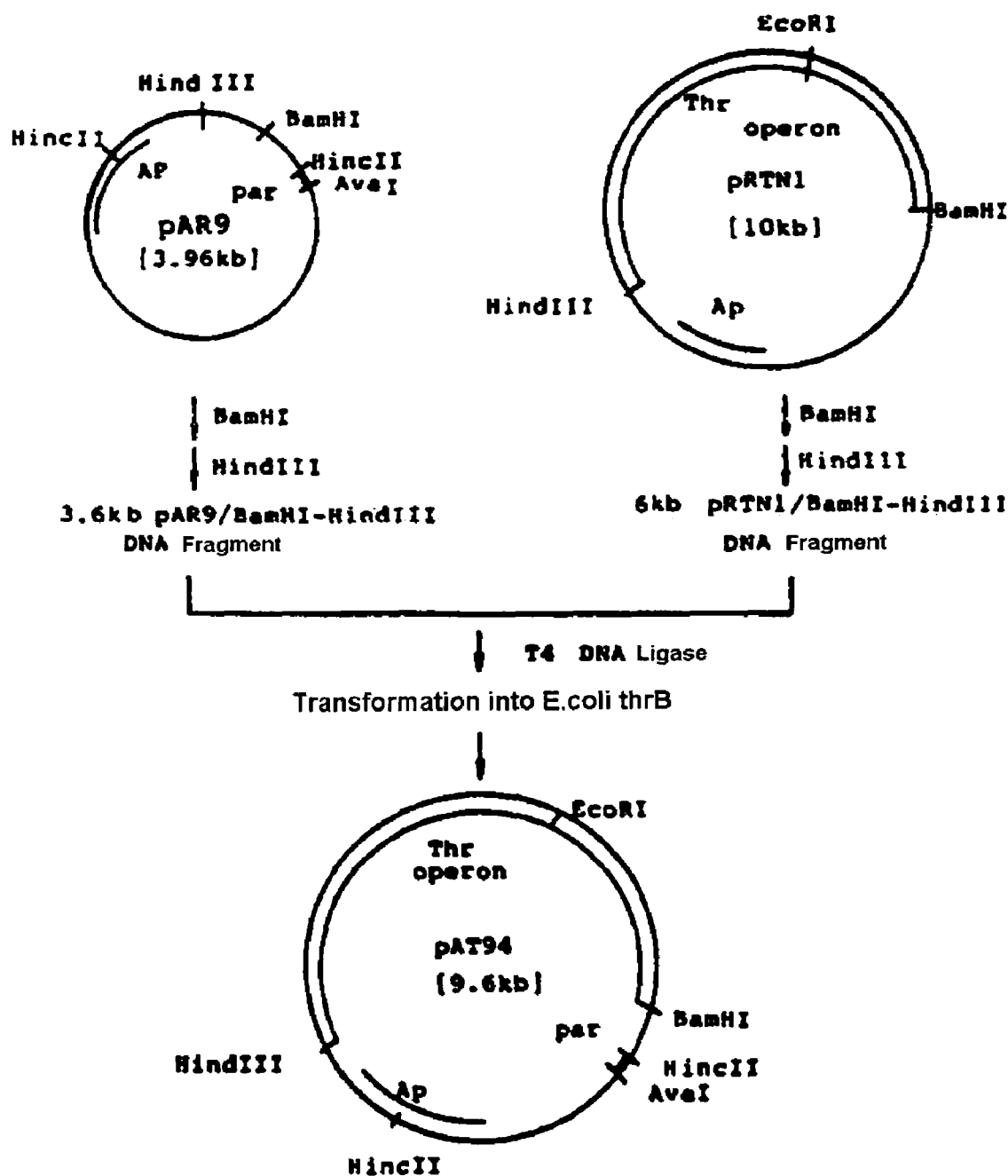
FIG. 1C depicts a process of constructing the recombinant plasmid pAT94.

The process of cloning the phosphoenolpyruvate carboxylase (ppc) gene is illustrated in FIG. 1A. The ppc gene was obtained from a threonine producing strain, TF 4076 (Accession Number KFCC 10718) deposited with the Korean Culture Center of Microorganisms (KCCM). The threonine producing strain, TF 4076, was produced according to the following procedures. *Escherichia coli* wild-type strains (*E.coli* W3110) (NEB, KoramBioTech, Korea) were suspended in a phosphate buffer (pH 7.0) or a cistrate buffer (pH 5.5) and artificially mutated by adding 100-500 mg/l of N-methyl-N'-nitro-N-nitrosoguanidin (hereafter, 'NTG'). Among the mutant strains, methionin analogs-resistant colonies were selected by culturing in minimal agar media comprising 1-10 g/l of L-methionine analogs (DL-ethionine, norleucine, α-methylmethionine, L-methionine-D, L-sulphoximine). The colonies were cultured in nutrient agar media and centrifuged. L-threonine in the supernatant was quantitatively analyzed using HPLC to select L-threonine producing strains (TF0143). TF0143 strains were suspended in a 0.1M magnesium sulfate solution and mutated by irradiating UV for 30-150 seconds. The mutant strains were replica-plated and cultured in minimal agar media and methionine-added minimal agar media to select methionine-auxotrophic strains. Among them, L-threonine producing strains TF0670 were isolated after culturing with agitation and quantitative analysis. TF0670 strains were artificially mutated by using NTG. Among the mutant strains, L-threonine analogs-resistant colonies were selected by culturing in minimal agar media comprising 1-10 g/l of L-threonine analogs (α-amino-β-hydroxy valeric acid (hereafter, 'AHV') and DL-threonine hydroxamate). As described above, L-threonine in the cultured media was quantitatively analyzed using HPLC to select L-threonine producing strains (TF1148). The strains were mutated using NTG to select strains that are resistant to a high concentration (15-30 g/l) of L-threonine analogs, and L-threonine in the cultured media was quantitatively analyzed using HPLC to select strains that produce L-threonine with a higher yield (TF1299). The strains TF1299 were mutated using UV. The mutant strains were replica-plated and cultured to select isoleucine-leaky auxotrophic strains, which grow slowly in methionine-added minimal agar media but grow well in methionine and isoleucine-added minimal agar media. Among them, TF2387 strains that produce L-threonine with a high yield were isolated after culturing with agitation and quantitative analysis. TF2387 strains were artificially mutated using NTG. Among the mutant strains, L-lysine analogs-resistant colonies were selected by culturing in minimal agar media comprising 1-10 g/l of L-lysine analogs (S-(2-aminoethyl)-L-cysteine (hereafter, 'AEC') and r-methyl-L-lysine (hereafter, 'ML')). Among them, TF3057 strains that produce L-threonine with a high yield were isolated after culturing with agitation and quantitative analysis. The strain TF3057 were mutated using NTG and cultured in methionine and isoleucine-added minimal agar media comprising 1-10 g/l of α-amino butyric acid, analogs of L-valine and L-isoleucine to select α-amino butyric acid-resistant strains. After culturing with agitation and quantitative analysis, *E.coli* TF4076, which produces L-threonine with the highest yield of all other strains, was isolated. FIG. 1C depicts a process of constructing a recombinant plasmid pAT94.

A chromosomal DNA was isolated from the TF 4076 strain, digested with restriction enzyme Sal I, and subjected to electrophoresis to selectively isolate 4-5 kb DNA fragments. The ppc gene was amplified by using the isolated DNA fragments as templates and using primer 1 (5'-aggaat-tcttccgcagcatttgacgtcac-3'(SEQ ID NO. 1)) and primer 2 (5'-aggaagcttttagccggtattacgcatacc-3'(SEQ ID NO. 2)). The amplified product was digested with EcoR I and Hind III and subjected again to electrophoresis to finally isolate a 2.8 kb ppc gene fragment. A 7.6 kb pBRINT-TsGm, a kind of pBRINT-Ts vectors, from the National University of Mexico was used for cloning (Sylvie Le Beatriz et al., 1998, pBRINT-Ts: *A plasmid family with a temperature-sensitive replicon, designed for chromosomal integration into the lacZ gene of Escherichia coli., Gene.*, 223, pp. 213-219). pBRINT-TsGm was double digested with the same restriction enzymes, EcoR I and Hind III, and ligated with the isolated ppc gene fragment by T4 DNA Ligase. *E.coli* strain DH5α was transformed with the ligated DNA by electroporation and cultured on LB solid medium [yeast extract 5 g/L; bactotryptone 10 g/L; sodium chloride 10 g/L; bactoagar 1.7%; pH 7.0] containing antibiotics, 50 mg/L of carbenicillin and 5 mg/L of gentamycin. Next, single colonies were collected. Single colonies were cultivated on LB media containing the same antibiotics to isolate plasmids from the grown strains. The size of each plasmid was primarily identified and double digested with EcoR I and Hind III to isolate a 2.8 kb DNA fragment. The resulting DNA fragments were identified to thereby complete construction of a recombinant plasmid pGmPPC (10.7 kb) containing the ppc gene.

EXAMPLE 2

Chromosomal DNA Integration Vector with Threonine Operon and ppc Gene

Recombinant plasmid vector pAT94 (KCCM 10018, Korean Patent Application No. 92-24732) deposited on Dec. 2, 1992 with the Korean Culture Center of Microorganisms (KCCM) under the Budapest Treaty was used for the threonine operon, and recombinant plasmid pGmPPC from Example 1 was used for the ppc gene. The recombinant plasmid vector pAT94 was constructed according to the following procedures. Plasmids pSC101 and pBR322 were isolated from *E.coli* JM103 (NEB, KoramBioTech, Korea) using a conventional alkaline lysis method and ultra-centrifugation (Molecular Cloining, 2nd ed., Sambrook, J., E. T. Fritch, and T. Maniatis). Plasmid pSC101 was completely digested with restriction enzyme HincII, electrophoresed on agarose gel, and purified using Geneclean II kit (Bio101) to obtain 2.8 kb of DNA fragment. The purified 2.8 kb pSC101/HincII fragment was digested with restriction enzyme Ava I, electrophoresed, and purified using Geneclean II kit to obtain 0.37 kb of a pSC101/HincII/Ava I DNA fragment (par region). Plasmid pBR322 was digested with restriction enzyme Ava I to obtain 4.36 kb of a pBR322/Ava I fragment, partially digested with restriction enzyme HincII, electrophoresed on an agarose gel, and purified using Geneclean II kit to obtain 3.59 kb of DNA fragment. The 0.37 kb pSC101/HincII/Ava I fragment and 3.59 kb pBR322/Ava I/HincII fragment were ligated using T4 DNA ligase and inserted into *E.coli* JM103 using a conventional electroporation method. The recombinant plasmid was isolated from the transformant using a conventional alkaline lysis method. The plasmid DNA was digested with several restriction enzymes and electrophoresed on an agarose gel to identify the size of fragments. As a result, plasmid pAR9 (3.96 kb) having 0.37 kb of a par region and 3.59 kb of a pBR322/Ava I/HincII fragment was obtained. FIG. 1B depicts a process of constructing the recombinant plasmid pAR9.

Figure 2:
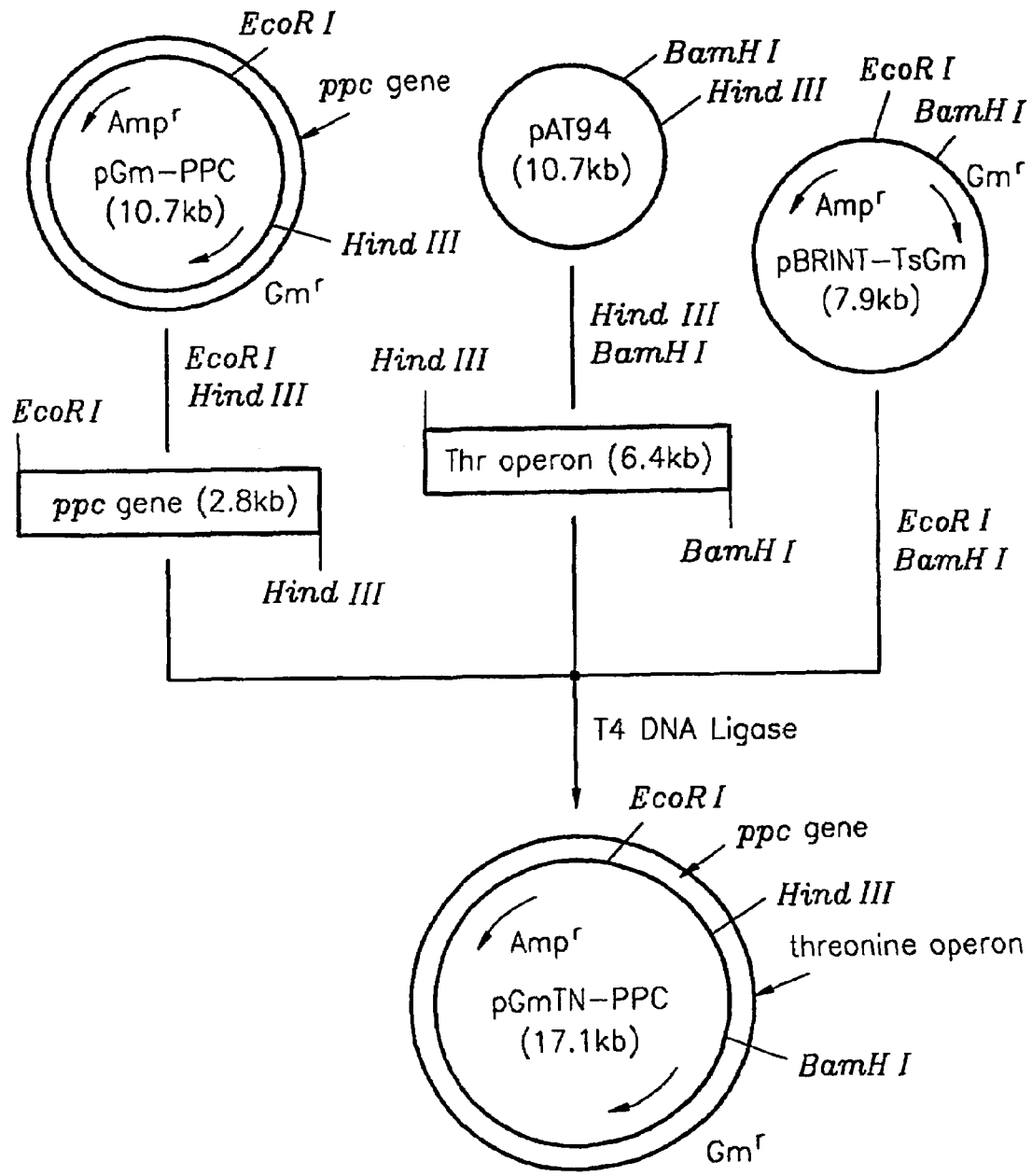
FIG. 2 depicts the construction of a recombinant plasmid pGmTN-PPC cloned with the ppc gene and the threonine operon.

Plasmids pRTN1 was isolated from *E.coli* JM109 (NEB, KoramBioTech, Korea) using conventional alkaline lysis. pTRN1 was double digested with restriction enzymes BamHI and HindIII, electrophoresed, and purified using Geneclean II kit to obtain 6 kb of a BamHI-HindIII DNA fragment having a threonine operon. Plasmid pAR9 was isolated from *E.coli* JM103 using conventional alkaline lysis, double digested with restriction enzymes BamHI and HindIII, electrophoresed, and purified using Geneclean II kit to obtain 3.6 kb of a BamHI-HindIII DNA fragment having a par region. 6 kb of a BamHI-HindIII DNA fragment with a threonine operon and 3.6 kb of a BamHI-HindIII DNA fragment with a par region were ligated with T4 DNA ligase and transformed into *E.coli* thrB host as described above to obtain an ampicilin-resistant transformant. Plasmids DNA were isolated from the transforamt, digested with several restriction enzymes, and analysed using electrophoresis. As a result, plasmid pAT94 (9.6 kb) having 6 kb of a BamHI-HindIII DNA fragment with a threonine operon and 3.6 kb of BamHI-HindIII DNA fragment with a par region was obtained.

pBRINT-TsGm, a kind of pBRINT-Ts vectors, from the National University of Mexico was used as a chromosomal DNA integration vector (Sylvie Le Beatriz et al., 1998, pBRINT-Ts: *A plasmid family with a temperature-sensitive replicon, designed for chromosomal integration into the lacZ gene of Escherichia coli., Gene.*, 223, pp. 213-219). A process of construction of a recombinant plasmid is illustrated in FIG. 2. pAT94 was double digested with restriction enzymes Hind III and BamH I, and 6.4 kb threonine operon DNA fragments were isolated from the double digest by electrophoresis. pGmPPC was double digested with Hind III and EcoR I to isolate 2.8 kb ppc gene fragments. pBRINT-TsGm plasmid vector was digested with EcoR I and BamH I, and completely digested DNA fragments were isolated by the same method. The resulting plasmid vector digest, isolated threonine operon DNA fragments, and ppc gene fragments were mixed and ligated by T4 DNA ligase. *E.coli* strain DH5a was transformed with the ligated product by electroporation and cultured on LB solid medium [yeast extract 5 g/L; bactotryptone 10 g/L; sodium chloride 10 g/L; bactoagar 1.7%; pH 7.0] containing antibiotics, 50 mg/L of carbenicillin and 5 mg/L of gentamycin. Next, single colonies were collected. Single colonies were cultivated on LB media containing the same antibiotics to isolate plasmids from the grown strains. The size of each plasmid was primarily identified and double digested with EcoR I and BamH I to isolate 9.2 kb and 7.9 kb DNA fragments. The resulting DNA fragments were identified to thereby complete construction of a recombinant plasmid pGmTN-PPC (17.1 kb) containing the threonine operon and ppc gene.

EXAMPLE 3

Screen of Strain Integrated with Chromosomal Recombinant-plasmid

TF4076, a threonine producing strain, was transformed with the recombimant plasmid pGmTN-PPC isolated from *E.coli* strain DH5α, cultured on LB solid medium [yeast extract 5 g/L; bactotryptone 10 g/L; sodium chloride 10 g/L; bactoagar 1.7%; pH 7.0] containing 5 mg/L of gentamycin, and cultivated for 60 hours at 30° C. Each single colony was inoculated into 0.5 mL of LB and incubated for 4 hours at 30° C. An aliquot of the culture was transferred into 10 mL of LB, incubated for 6 hours at 30° C. and then overnight at 37° C. A $10^{-3}$-$10^{-6}$ dilution of the culture was inoculated on LB solid medium containing 5 mg/L of gentamycin. At this time, 12 µL of IPTG (0.1M) and 60 µL of X-gal (2%) were also inoculated on the LB solid medium. After 24-hour incubation at 44° C., recombinant strains were screened for white colonies sensitive to carbenicillin, which cannot grow on the LB solid medium containing 15 mg/L of carbenicillin. The screened recombinant stains confirmed the presence of the expected plasmids, in which the ppc gene and threonine operon were integrated into the lacZ gene site of the chromosomal DNA of each strain.

EXAMPLE 4

Comparison of Threonine Productivity in Flask Cultivation for Recombinant Strains Thirty single colonies of the recombinant strains with recombinant plasmids integrated into their chromosome were screened for threonine productivity comparisons using threonine titer media in Erlenmeyer flasks. The composition of the threonine titer medium used in each case is shown in Table 1. Colonies were cultured on LB solid media overnight in a 32° C. incubator. 20 mL of the titer medium was inoculated with a loopful of each culture and incubated at 32° C., 250 rpm for 48 hours. The results of the analysis are shown in Table 2. All thirty colonies of recombinant strains show excellent productivity, including eight colonies that produced 26 g/L or greater threonine, compared to the host strain, TF 3076, which produced 20 g/L of threonine. The recombinant strain, which recorded the highest threonine productivity at 27 g/L with a 35% higher yield than the host strain, was named "pGmTN-PPC12". The strain pGmTN-PPC12 was deposited Jan. 5, 2001 with the Korean Culture Center of Microorganisms (KCCM) under the Budapest Treaty and was given Accession Number KCCM 10236.

TABLE 1

Composition of Threonine Titer Medium

| Component | Amount per liter |
|---|---|
| Glucose | 70 g |
| $(NH_4)_2SO_4$ | 28 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| Calcium carbonate | 30 g |
| L-methionine | 0.15 g |
| Yeast extract | 2 g |
| PH 7.0 | |

TABLE 2

Results of Flask Titer Test for Recombinant Strains

| L-threonine concentration | 20-22 g/L | 22-24 g/L | 24-26 g/L | 26 g/L or greater |
|---|---|---|---|---|
| Colony Counts | 7 | 6 | 9 | 8 |

EXAMPLE 5

Comparison of Threonine Productivity using Fermentor

Threonine productivity in a fermentor was compared between recombinant strain pGmTN-PPC12 selected from its highest threonine titer from Example 4 and host strain TF4076. The initial medium composition used is shown in Table 3. LB media further containing per liter 10 g of glucose and 0.1 g of L-methionine were used for seed culture, and an initial volume of inoculation into a fermentor was determined at 3-5% by volume of a target initial culture. Glucose was added at a final concentration of 5% by weight each time, over 6 times in total, along with $KH_2PO_4$ at 1% by weight. Here, each addition of glucose was determined by deletion of glucose. The initial volume of the culture was 1.5L and the final volume of the culture was 3.0L. A total concentration of glucose added through fermentation was 250 g/L. During fermentations, the medium was stirred at 700-1000 rpm, temperature was controlled at 32° C., and pH was adjusted at 7.0 with 25-28% ammonia water. Air-flow velocity was adjusted at 0.1 vvm. The results are shown in Table 4. As shown in Table 4, the host strain TF4076 produces 75.3 g/L of threonine with a yield of 30.1% with respect to glucose consumption. In contrast, recombinant strain pGmTN-PPC12 produces 102 g/L threonine with a yield of 40.8%, which is 35.4% higher than the host strain TF4076. In addition, a similar fermentation pattern as the host strain was observed on the recombinant strain, without reduction in sugar consumption during fermentation, which often appears on recombinant strains due to growth inhibition.

TABLE 3

Initial Medium Composition in 5-L Fermentor

| Component | Amount per liter |
|---|---|
| Glucose | 50 g |
| $KH_2PO_4$ | 4 g |
| $(NH_4)_2SO_4$ | 6 g |
| Yeast extract | 3 g |
| $MgSO_4 \cdot 7H_2O$ | 2 g |
| L-methionine | 1 g |
| $FeSO_4 \cdot 7H_2O$ | 40 mg |
| $MnSO_4 \cdot 8H_2O$ | 10 mg |
| $CaCl_2 \cdot 2H_2O$ | 40 mg |
| $CoCl_2 \cdot 6H_2O$ | 4 mg |
| $H_3BO_3$ | 5 mg |
| $Na_2MoO_4 \cdot 2H_2O$ | 2 mg |
| $ZnSO_4 \cdot 7H_2O$ | 2 mg |
| PH 7.0 | |

TABLE 4

Results of Fermentative Production of Threonine by Recombinant Strains

| Strain | Threonine (g/L) | Fermentation Time (hr) | Yield (%) |
|---|---|---|---|
| TF4076 | 75.3 | 78 | 30.1 |
| pGmTN-PPC12 | 102 | 77 | 38.0 |

As described above, according to the present invention, two or more ppc genes and threonine operons are included in the chromosomal DNA to thereby enhance the expression of the ppc gene, which encodes an enzyme to convert phosphoenolpyruvate to a threonine biosynthesis precursor, oxaloacetete, and the genes encoding enzymes involved in the synthetic pathway of threonine from oxaloacetate, including thrA (aspartokinase1-homoserine dehydrogenase), thrB (homoserine kinase), and thrC (threonine synthase). The present invention can remarkably improve productivity of L-threonine by 35% higher than the host strain.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A method of producing L-threonine, comprising:

constructing a recombinant chromosomal DNA integration system comprising one or more copies of each of a nucleic acid encoding phosphoenolpyruvate carboxylase which is obtained using PCR primers of SEQ ID NO: 1 and SEQ ID NO: 2 from *Escherichia coli* strain TF 4076 Accession No. KFCC 10718 and a threonine operon from a microorganism belonging to the *Eseherichia* or *Corynebacterium* genus resistant to threonine analogs, lysine analogs, isoleucine analogs, or methionine analogs;

introducing the recombinant chromosomal DNA integration system into a microorganism belonging to the *Escherichia* genus to integrate the one or more additional copies into the lacZ gene site of the *Eseherichia* chromosomal DNA while the microorganism's inherent phosphoenolpyruvate carboxylase gene and threonine operon remain;

culturing the transformed *Escherichia* with substrates to produce L-threonine; and isolating the produced L-threonine.

2. The method of claim 1, wherein the nucleic acid encoding phosphoenolpyruvate carboxylase of the recombinant chromosomal DNA integration vector is obtained from the chromosome of a threonine producing *E.coli* strain, TF4076, of Accession No. KFCC 10718 by polymerase chain reaction (PCR), and the threonine operon of the recombinant chromosomal DNA integration vector is cloned from said *E.coli* strain TF4076, wherein the obtained nucleic acid encoding phosphoenolpyruvate carboxylase and the cloned threonine operon are incorporated into the chromosome of the host strain *E.coli* TF4076.

3. The method of claim 1, wherein the microorganism is constructed with recombinant plasmid pGmTN-PPC of FIG. 2.

* * * * *